(12) United States Patent
Pan et al.

(10) Patent No.: US 10,042,160 B2
(45) Date of Patent: Aug. 7, 2018

(54) ANNULAR SCANNING DEVICE FOR OPTICAL TOMOGRAPHY SCANNING AND IMAGING SYSTEM

(71) Applicant: NATIONAL CENTRAL UNIVERSITY, Taoyuan County (TW)

(72) Inventors: Min-Chun Pan, Taoyuan County (TW); Jhao-Ming Yu, Taichung (TW); Liang-Yu Chen, Taoyuan (TW); Min-Cheng Pan, New Taipei (TW); Ya-Fen Hsu, Taoyuan County (TW)

(73) Assignee: National Central University, Taoyuan (TW)

( * ) Notice: Subject to any disclaimer, the term of this patent is extended or adjusted under 35 U.S.C. 154(b) by 424 days.

(21) Appl. No.: 14/714,463

(22) Filed: May 18, 2015

(65) Prior Publication Data
US 2016/0231100 A1    Aug. 11, 2016

(30) Foreign Application Priority Data
Feb. 9, 2015    (TW) .............................. 104104301 A

(51) Int. Cl.
*A61B 6/00* (2006.01)
*G02B 26/10* (2006.01)
*A61B 5/00* (2006.01)

(52) U.S. Cl.
CPC .......... *G02B 26/103* (2013.01); *A61B 5/0066* (2013.01); *A61B 5/0091* (2013.01)

(58) Field of Classification Search
CPC ........................... A61B 5/0059; A61B 5/0084
See application file for complete search history.

(56) References Cited

U.S. PATENT DOCUMENTS

| | | | | |
|---|---|---|---|---|
| 6,081,322 A | * | 6/2000 | Barbour | G01N 21/4795 356/337 |
| 2014/0236003 A1 | * | 8/2014 | Hielscher | A61B 5/0091 600/428 |

OTHER PUBLICATIONS

Jhao-Ming Yu, Liang-Yu Chen, Min-Cheng Pan, Ya-Fen Hsu, and Min-Chun Pan; Implementation of 3D Prostrate Ring-Scanning Mechanism for NIR Diffuse Optical Imaging-Phantom Validation; Optical Tomography and Spectroscopy of Tissue XI, Proc. of SPIE vol. 9319.

* cited by examiner

*Primary Examiner* — Hien Nguyen
(74) *Attorney, Agent, or Firm* — Rosenberg, Klein & Lee

(57) ABSTRACT

The present invention relates to an annular scanning device for optical tomography scanning and imaging system, which comprises a carrying base, a rotating member, a plurality of optical channel modules, and a driving module. The rotating member is disposed on the carrying base. The plurality of optical channel modules are disposed annularly on the rotating member and connected to the rotating member. When the driving module drives the rotating member to rotate, a plurality of optical channel assemblies of the plurality of optical channel modules move towards or away from the center of the rotating member for adjusting the distance between the plurality of optical channel assemblies and an object under test.

15 Claims, 9 Drawing Sheets

ANNULAR SCANNING DEVICE FOR OPTICAL TOMOGRAPHY SCANNING AND IMAGING SYSTEM

FIELD OF THE INVENTION

The present invention relates generally to an annular scanning device, and particular to an annular scanning device for optical tomography scanning and imaging system.

BACKGROUND OF THE INVENTION

As modern technologies advance, diseases of civilization become popular increasingly. The cancer is one of the diseases of civilization. In daily lives, people may contact as many as 17 kinds of chemicals that increase the probability of suffering from cancers. The exhaust generated by diesel and petroleum automobiles, secondhand smoke, and scorched food contain the carcinogens benzene and butadiene. Fire retardants in plastics and paint, anti-dust fabrics, and cleaning solvent also contain carcinogenic chemicals.

Among the cancers as described above, the breast cancer is the most common cancer for females. There are approximately 500 thousand people died of breast cancer worldwide. According to the medical statistic report of Taiwan in 2003, it is found that the breast cancer was the fourth of the death rate of female cancers. The age of occurring breast cancer is around 40 to 50 years old for eastern females and 30 to 40 years old for western ones. The breast cancer is a cancer easily found in the early stage. If tumors are found in the breast, people are normally bashful to tell others. With the fear of breast resection, the opportunity of cure is delayed. In fact, most tumors are benign; treating breast cancer does not necessarily mean losing the whole breast. It is found from recent clinical treatment that the average 10-year survival rate for breast cancer reaches 60%; the survival rate after treatment for the first-stage breast cancer reaches 80%; the survival rate after treatment for the zero-stage breast cancer even approaches 100%. Accordingly, it is extremely important to find and cure early.

There are many ways to prevent breast cancer. In addition to self-examination, there are still breast photography and palpation by physicians. The best method is to do routine examination on items related to breast cancer in hospitals. Most of current hospitals adopt optical tomography scanning and imaging systems to scan breasts and produce breast images. An optical tomography scanning and imaging system scans breasts by using a plurality of optical channel modules. Nonetheless, the distance between the plurality of optical channel modules and breasts is fixed. If the examinee's breasts are smaller, the distance between the plurality of optical channel modules and breasts is greater; if the examinee's breasts are larger, the distance between the plurality of optical channel modules and breasts is smaller. Either the distance greater or smaller, the examination result is influence and leading to reduction in the accuracy of examination. The main cause is that the distance between the plurality of optical channel modules and breasts is not adjustable. In the above examination, the breast examination is taken as an example. An optical tomography scanning and imaging system can be applied to the examination of other body parts. Then the problem described above also occurs.

SUMMARY

An objective of the present invention is to provide an annular scanning device for optical tomography scanning and imaging system. A plurality of optical channel modules thereof are assembled at a rotating member. Thereby, the plurality of optical channel modules can be disassembled from and assembled to the rotating member rapidly. Adjustment can be performed according to examination requirements.

Another objective of the present invention is to provide an annular scanning device for optical tomography scanning and imaging system. The plurality of optical channel modules measure an object under test of an examinee through a non-contact or slightly contact method. Thereby, the examinee can feel comfortable and safe during the examination process.

Still another objective of the present invention is to provide an annular scanning device for optical tomography scanning and imaging system. The distance between the plurality of optical channel modules and the object under test can be maintained fixed for confirming the shape of the object under test and thus facilitating future image reconstruction.

The present invention provides an annular scanning device for optical tomography scanning and imaging system, which comprises a carrying base, a rotating member, a plurality of optical channel modules, and a driving module. The carrying base includes a first hole and a plurality of guiding grooves. The plurality of guiding grooves are disposed annularly about the first hole on the carrying base. The rotating member is disposed on the carrying base and includes a second hole and a plurality of positioning openings. The second hole corresponds to the first hole. The plurality of positioning openings correspond to the plurality of guiding grooves, respectively. The plurality of optical channel modules are disposed between the rotating member and the plurality of positioning openings and include an optical channel assembly and a sliding base, respectively. The optical channel assembly is disposed on the sliding base. One end of the sliding base corresponds to the positioning opening and the guiding groove. The driving module is disposed on the carrying base and connected to the rotating member. The driving module drives the rotating member to rotate. The rotating member drives the plurality of sliding bases to slide on the rotating member. The plurality of sliding bases drive the plurality of optical channel assemblies to move towards or away from the direction of the second hole.

DETAILED DESCRIPTION

In order to make the structure and characteristics as well as the effectiveness of the present invention to be further understood and recognized, the detailed description of the present invention is provided as follows along with embodiments and accompanying figures.

Figure 1A:
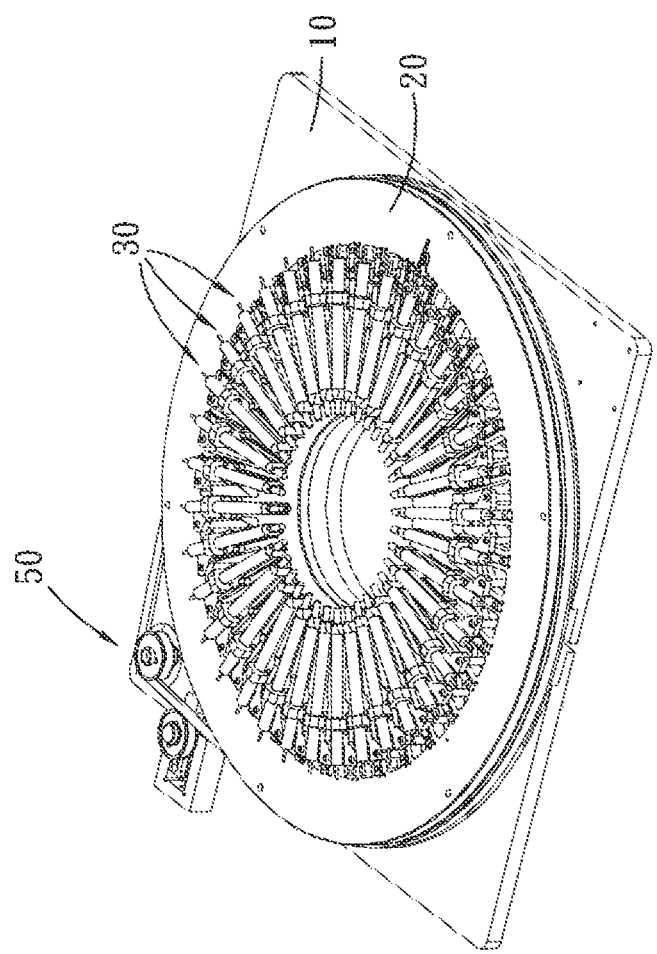
FIG. 1A shows a schematic diagram of the annular scanning device according the first embodiment of the present invention.
Figure 1B:
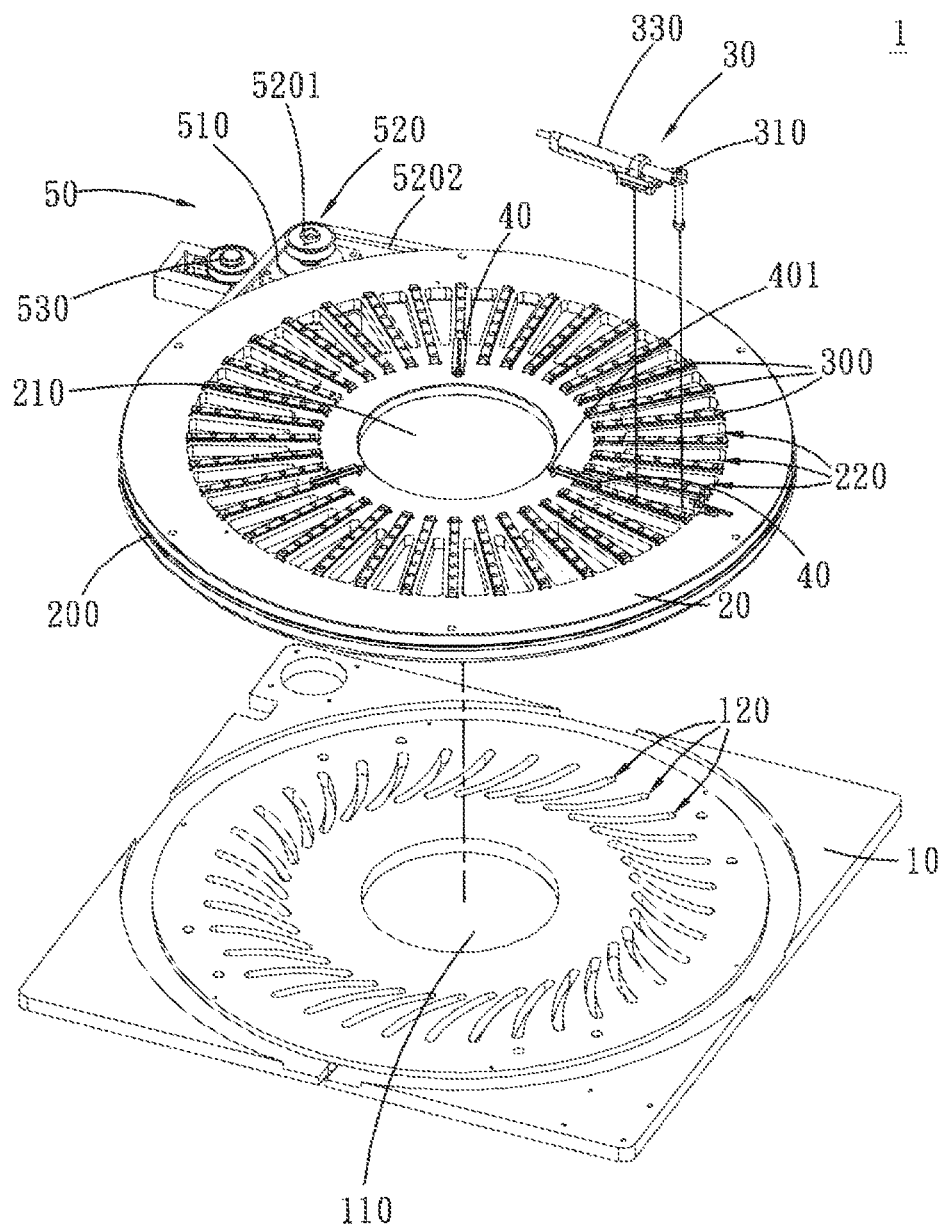
FIG. 1B shows an assembly diagram of the annular scanning device according the first embodiment of the present invention.
Figure 1C:
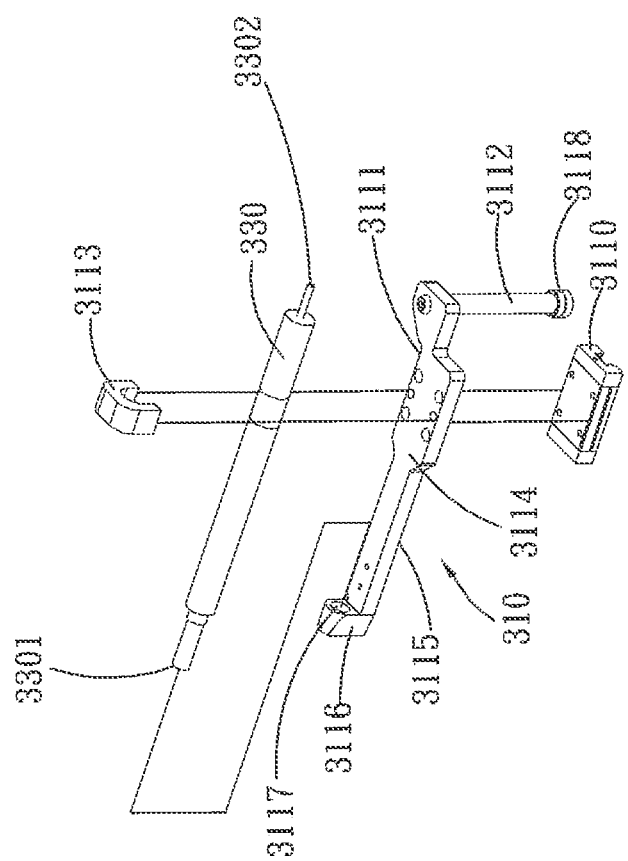
FIG. 1C shows an assembly diagram of the optical channel module according the first embodiment of the present invention.

Please refer to FIGS. 1A to 1C, which show a schematic diagram, an assembly diagram of the annular scanning device and an assembly diagram of the optical channel module according the first embodiment of the present invention. As shown in the figures, the present embodiment provides an annular scanning device 1 for optical tomography scanning and imaging system, which comprises a carrying base 10, a rotating member 20, a plurality of optical channel modules 30, and a driving module 50.

The carrying base 10 includes a first hole 110 and a plurality of curved guiding grooves 120. The plurality of guiding grooves 120 are disposed annularly about the first hole 110 on the carrying base 10. In other words, the plurality of guiding grooves 120 surround the first hole 110. The rotating member 20 includes a second hole 210 and a plurality of positioning openings 220. The plurality of positioning openings 220 are disposed annularly about the second hole 210 on the rotating member 20. When the rotating member 20 is disposed on the carrying base 10, the second hole 210 correspond to the first hole 110, and the plurality of positioning openings 220 correspond to the plurality of guiding grooves 120, respectively. The plurality of optical channel modules 30 are disposed on the rotating member 20 and between the plurality of positioning openings 220.

Each optical channel module 30 includes a sliding track 300, a sliding base 310, and an optical channel assembly 330. The plurality of sliding tracks 300 are disposed between the plurality of positioning openings 220 of the rotating member 20. The sliding base 310 of each optical channel module 30 is disposed slidably on the corresponding sliding track 300. One end of the sliding base 310 is disposed inside the positioning opening 220 on the same side of the sliding track 300 and inside the guiding groove 120. The optical channel assembly 330 is disposed on the sliding base 310.

The sliding base 310 according to the present embodiment further comprises a sliding block 3110, a base body 3111, a guiding pillar 3112, and a fixing member 3113. The base body 3111 includes a first surface 3114 and a second surface opposite to the first surface 3114. The sliding block 3110 is disposed on the second surface 3115 of the base body 3111. The guiding pillar 3112 is disposed at the base body 311 and extends in the direction away from the second surface 3115 of the base body 3111. The base body 3111 includes a positioning part 3116 at one end. The positioning part 3116 includes a hole 3117. The optical channel assembly 330 is disposed on the first surface 3114 of the base body 3111. A first end of the optical channel assembly 330 passes through the hole 3117 of the positioning part 3116. The fixing member 3113 is disposed at the base body 3111 such that a second end of the optical channel assembly 330 is located between the fixing member 3113 and the base body 3111. The first end 3301 of the above optical channel assembly 330 can be a light output or a light receiver. The above sliding block 3110, the base body 3111, and the fixing member 3113 are assembled by locking, which means that the sliding bas 310 can be disassembled and assembled.

The sliding base 310 of each optical channel module 30 according to the present embodiment is wedged in the sliding track 300 via the sliding block 3110. Thereby, the sliding base 310 can be disassembled from the sliding track 300 rapidly as well as being assembled to the sliding track 300 rapidly. That is to say, the plurality of optical channel modules 30 can be disassembled. They can be loaded to the rotating member 30 rapidly. Alternatively, they can be disassembled from the rotating member 20 rapidly as well. Thanks to the rapid disassembling and assembling of the plurality of optical channel modules, the plurality of optical channel modules 30 can be disposed according the user's requirements. For example, the number of the plurality of optical channel modules 30 can be increased or reduced. Alternatively, the locations of the plurality of optical channel modules 30 can be adjusted.

Figure 2:
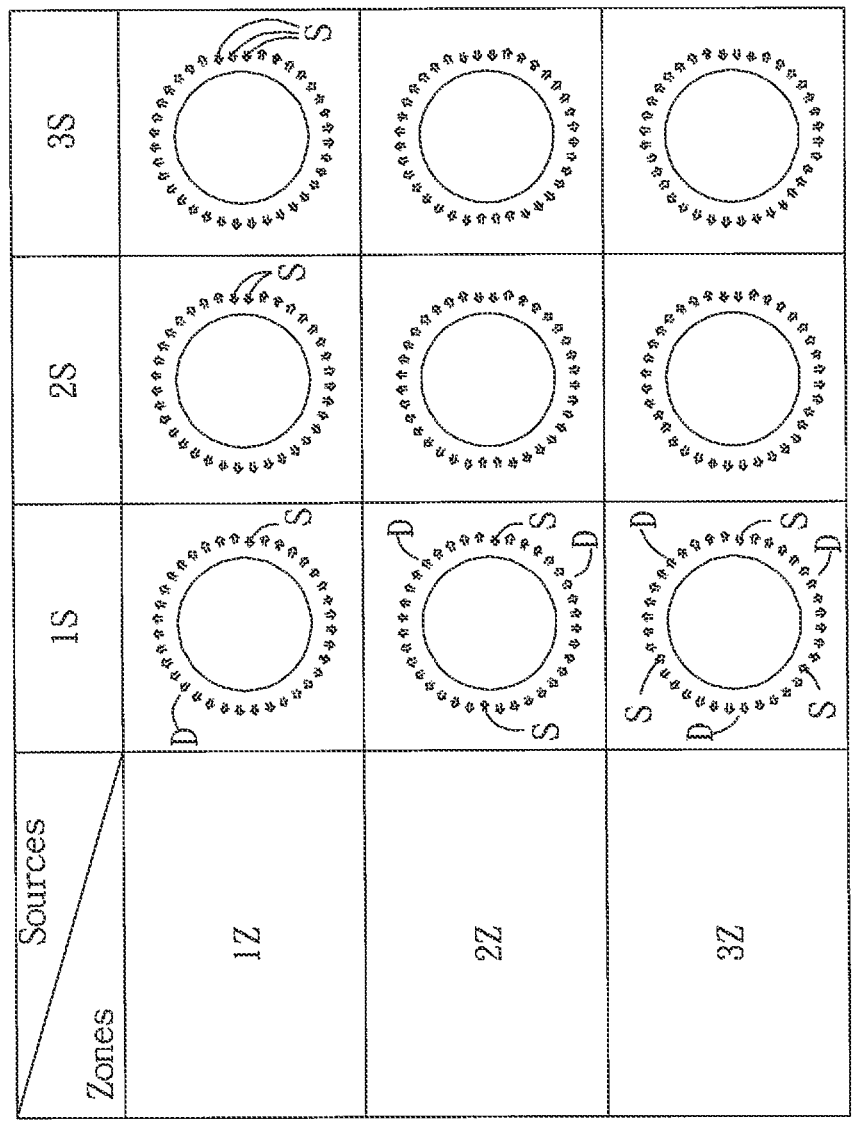
FIG. 2 shows a disposition diagram of the optical channel module according the first embodiment of the present invention.

Please refer to FIG. 2, which shows a disposition diagram of the optical channel module according the first embodiment of the present invention. As shown in the figure, the annular scanning device 1 according to the present embodiment comprises 36 optical channel modules 30. Some of the plurality of optical channel modules 30 are divided into at least a light-source set Z and at least detection set Z. At least an optical channel module in the detection set D is used for providing a detection light source; at least an optical channel module 30 in the detection set D is used for receiving the reflected detection light source. According to the present embodiment, 9 dispositions of the optical channel modules 30 are provided.

Here, the disposition of 1S3Z is used as an example. In this disposition, the plurality of optical channel modules 30 are divided into 3 light-source assemblies Z and 3 detection assemblies D. Each of the light-source assemblies Z includes an optical channel module 30. Hence, the rest 33 optical channel modules 30 are divided evenly into 3 detection assemblies D with each detection having 11 optical channel modules 30. The 3 light-source assemblies Z are separated evenly for providing the detection the detection light source to the center of the rotating member 20 from 3 directions uniformly. The number of the optical channel modules 30 of each light-source set Z can be certainly increased from one to two and above, such as the dispositions of 2S3Z and 3S3Z. As the number of the optical channel module 30 of each light-source set Z is increased, the number of the optical channel modules 30 in the plurality of detection assemblies D is decreased. The number of the light-source set Z is of course increased or reduced according to the user's requirements. In the present embodiment, the number of the light-source set Z is one, which is the minimum number. The number can be certainly increased to three or above. The disposition is not limited to the one provided by the present embodiment.

Figure 3A:
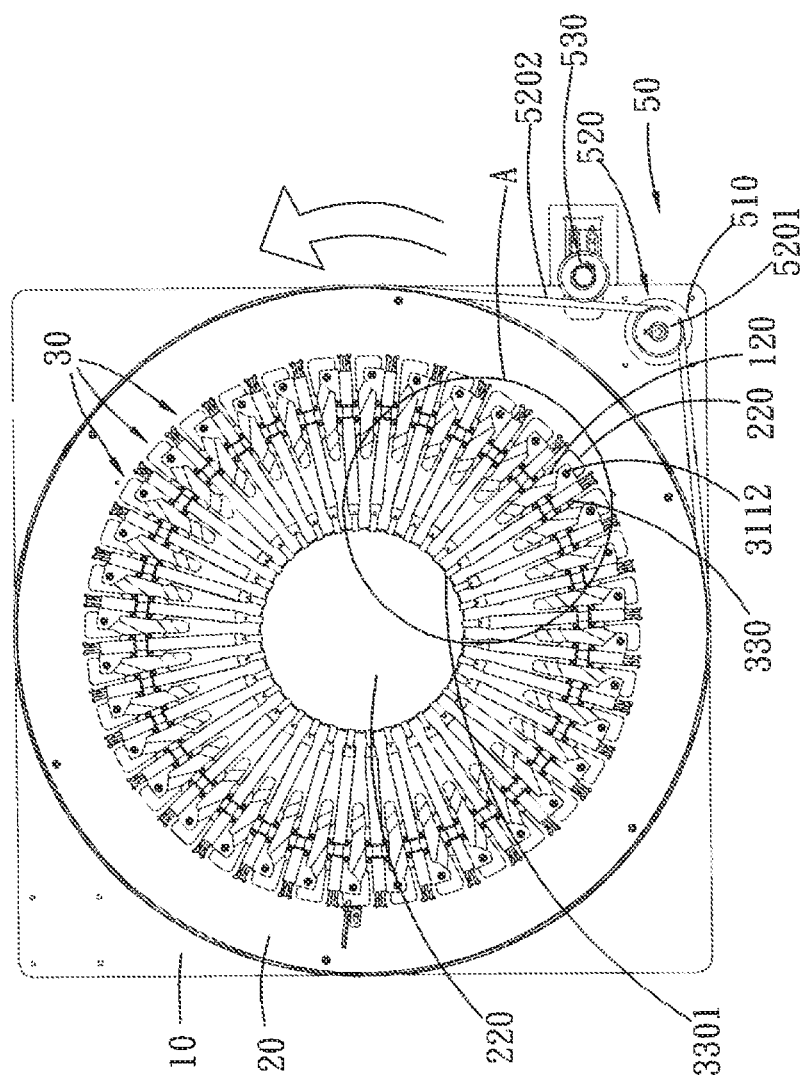
FIG. 3A shows a usage status diagram of the annular scanning device according the first embodiment of the present invention.
Figure 3B:
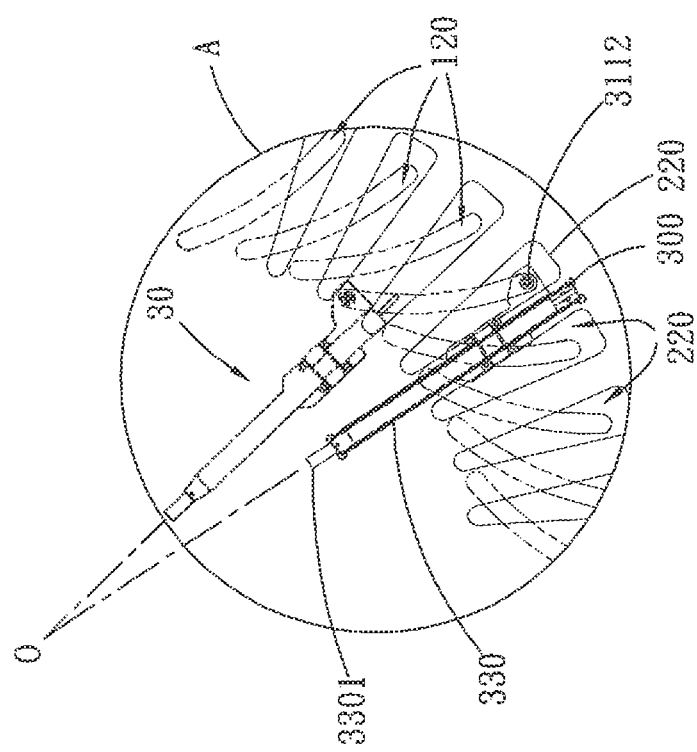
FIG. 3B shows an enlarged view of the region A in FIG. 3A.

Please refer to FIG. 3A and FIG. 3B, which show a usage status diagram of the annular scanning device according the first embodiment of the present invention and an enlarged view of the region A in FIG. 3A. As shown in the figures, the driving module 50 is connected with the rotating member for driving the rotating member 20 to rotate. As the rotating member 20 rotates, the plurality of positioning openings 220 of the rotating member 20 drives the plurality of guiding pillars 3112 passing through the plurality of positioning openings 220 so that each of the guiding pillars of the optical channel modules 30 moves along the corresponding guiding groove 120. The guiding pillar 3112 drives the corresponding sliding base 310 to slide on the corresponding sliding track 300, so that the sliding base 310 moves close to or away from the second hole 210. The sliding base 310 drives the optical channel assembly 330 disposed thereon to move close to or away from the second hole 210. The first end 3301 of each of the optical channel assemblies 330 aligns with the center O of the second hole 210. A bearing 3118 is disposed at one end of the guiding pillar 3113 located in the guiding groove, as shown in FIG. 1B. The bearing 3118 contacts the sidewall of the guiding groove 120. Thereby, when the guiding pillar 3112 moves along the guiding groove 120, the bearing 3118 reduces the friction between the guiding pillar 3112 and the guiding groove 120. Consequently, the guiding pillar 3112 can move in the guiding groove 1200 smoothly.

According to the present embodiment, the driving module 50 includes an actuator 510 and a transmission structure 520. The actuator 510 is disposed on the carrying base 10. The transmission structure 520 is connected to the actuator 510 and the rotating member 20. The transmission structure 520 according to the present embodiment includes a first transmission member 5201 and a second transmission member 5202. The transmission member 5201 is a roller and disposed at the actuator 510. The second transmission member 5202 is a belt and connected with the rotating member 20 and the first transmission member 5201. The second transmission ember 5202 is put around the peripheries of the rotating member 20 and the first transmission member 5201. The periphery of the rotating member 20 includes a trench 200, as shown in FIG. 1B, so that the second transmission member 5202 can be disposed in the trench 200 for avoiding coming off the rotating member 20 during rotation. As the actuator 510 drives the first transmission member 5201 to rotate, the first transmission member 5201 drives the second transmission member 5202 to rotate. The second transmission member 5202 drives the rotating member 20 to rotate. As a result, the driving module 50 effectively drives the rotating member 20 to rotate. According to the present embodiment, the actuator 510 is a stepping motor. Alternatively, other types of motors or other driving devices can be adopted as well. The driving module 50 can further include an auxiliary member 530. The auxiliary member 530 is an idler pulley and disposed on one side of the carrying base 10. The periphery of the auxiliary member 530 contacts the second transmission member 5202. When the second transmission member 5202 rotates, the auxiliary member 530 guides the rotation of the second transmission member 5202 for preventing the second transmission member 5202 from coming off the first transmission member 5201 and the rotating member 20 as well as facilitating smooth rotation of the second transmission member 5202.

Alternatively, the second transmission member 5202 of the transmission structure 520 can be a chain, not limited to being a belt, given that it can drive the first transmission member 5201 and the rotating member 20. In addition, the second transmission member 5202 can be omitted from the transmission structure 520 and the periphery of the first transmission member 5201 is adjacent to the periphery of the rotating member 20. When the first transmission member 5201 rotates, by using the friction between the first transmission member 5201 and the rotating member 20, the rotating member 20 is driven to rotate. Moreover, a gear can be even adopted as the first transmission member 5201. The periphery of the rotating member 20 includes gear teeth matched to the first transmission member 5201. Thereby, the first transmission member 5201 can also drives the rotating member 20 to rotate. In addition to the above description, the driving module 50 can alternatively include the actuator 510 only. Thereby, the actuator 510 will drive the rotating member 20 to rotate directly.

The second hole 210 of the rotating member and the first hole 110 of the carrying base 10 according to the present embodiment are used for accommodating an object under test, namely, the detection region of the plurality of optical channel modules 30. As the rotating member 20 rotates, the rotating member 20 drives the optical channel assemblies 330 of the plurality of optical channel modules 30 to move close to or away from the second hole 210 for adjusting the distance between the first end 3301 of the optical channel assembly 330 and the objects under test. Thereby, the optical channel assemblies 330 can detect the detection light source reflected form the object under test and improve the accuracy of detection.

Besides, please refer to FIG. 1B. A sensing member 40 is disposed at one or more of the plurality of optical channel modules 30. According to the present embodiment, the sensing member 40 is a photoelectric proximity switch disposed at the end of the sliding base 310 close to the second hole 210. A sensing end 401 of the sensing member 40 faces the second hole 210. The sensing end 401 aligns to the first end 3301 of the optical channel assembly 330. The sensing member 40 follows the optical channel assembly 330 to move close to or away from the second hole 210. The sensing member 40 can sense the distance between the sensing end 401 and the object under test. This distance is just the distance between the first end 3301 of the optical channel assembly 330 and the object under test. When the sensing member 40 senses that the distance between the first end 3301 of the optical channel assembly 330 and the object under test meets a predetermined value, the sensing member 40 generates a control signal and transmits the control signal to the driving module 50. The driving module 50 stops driving the rotating member 20 to rotate according to the control signal for stopping movement of the optical channel assembly 330 and maintaining the distance between the first end 3301 of the optical channel assembly 330 and the object under test to be the predetermined value. The predetermined value is the distance of the detection light source reflected by the object under test and receivable by the first end 3301 of the optical channel assembly 330.

The number of the sensing member 40 according to the present embodiment is preferably three or above. As shown in FIG. 3A, the plurality of sensing members 40 are distributed evenly around the second hole 210. As a consequence, the distance between the plurality of first ends 3301 of the plurality of optical channel assemblies 330 and the object under test in each direction can be senses, thereby controlling the distance between the first end 3301 of each optical channel assembly 330 and the object under test to be identical and increasing the overall detection accuracy. The number of the sensing members 40 can be increased by multiples of three. By distributing the sensing members 40 around the second hole 210 uniformly, the distance between the plurality of first ends 3301 of the plurality of optical channel assemblies 330 and the object under test can be sensed with accuracy.

Figure 4A:
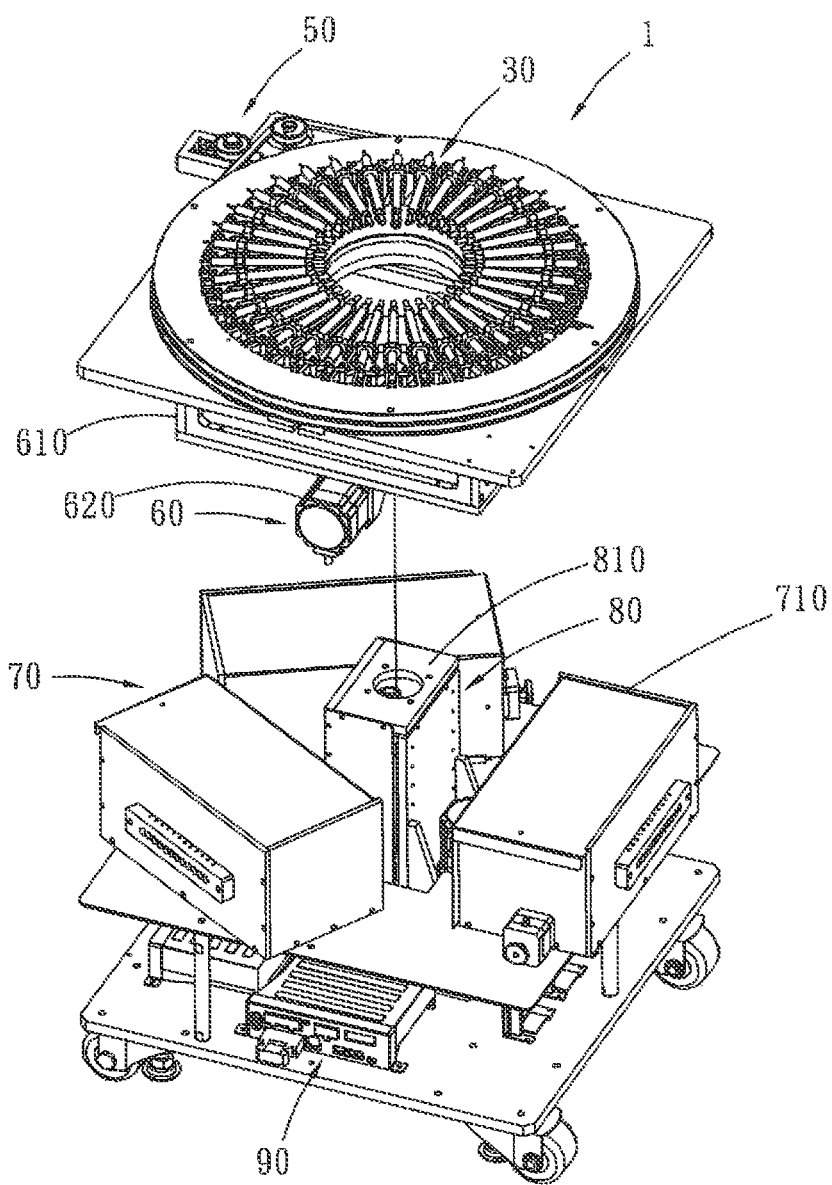
FIG. 4A shows an assembly diagram of the optical tomography scanning and imaging system according the second embodiment of the present invention.
Figure 4B:
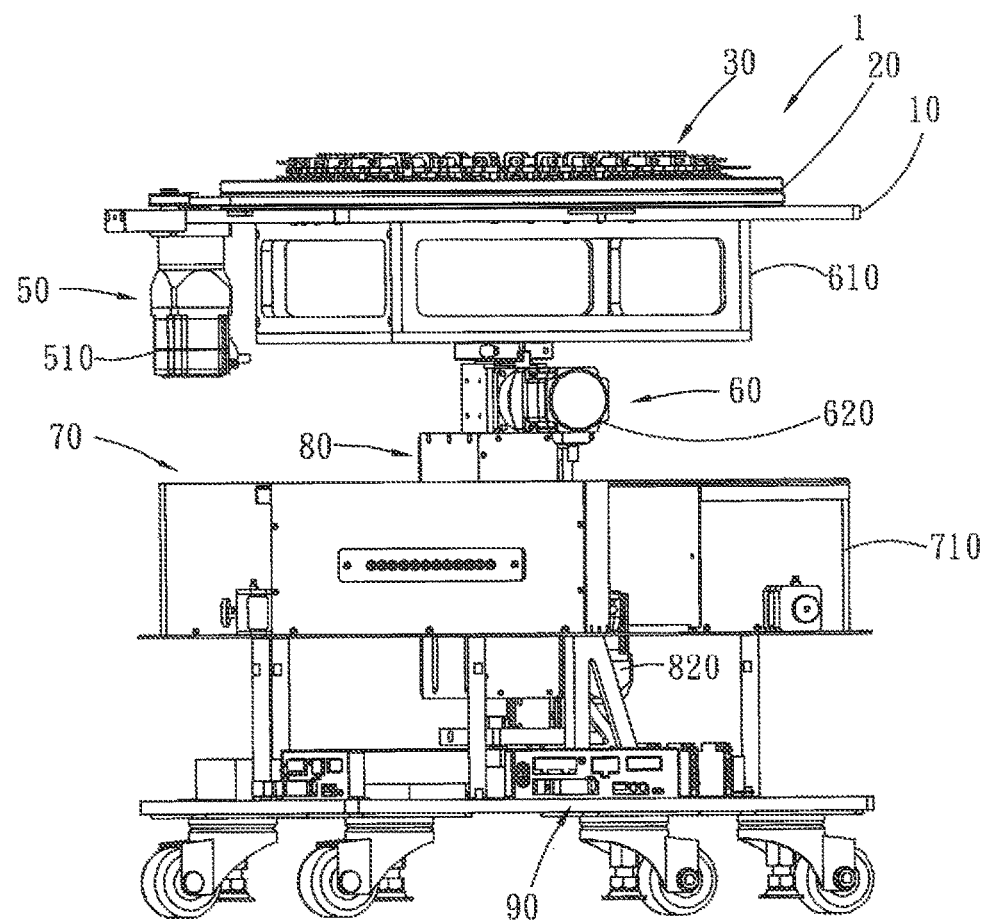
FIG. 4B shows a schematic diagram of the optical tomography scanning and imaging system according the second embodiment of the present invention.

Please refer to FIG. 4A and FIG. 4B, which show an assembly diagram and a schematic diagram of the optical tomography scanning and imaging system according the second embodiment of the present invention. As shown in the figures, the annular scanning device 1 according to the above embodiment is applied to an optical tomography scanning and imaging system 2 in the present embodiment. In addition to the annular scanning device 1, the optical tomography scanning and imaging system 2 according to the present embodiment further comprises a rotating module 60, a photodetection module 70, a lifting module 80, and a light-source module 90. The rotating module 60 includes a rotating frame 610 and an actuator 620. The rotating frame 610 is disposed on the carrying base 10 and opposite to the rotating member 20. The actuator 620 is connected to the center of the rotating frame 610 for driving the rotating frame 610 to rotate and thus further driving the carrying base 10, the rotating member 20, and the plurality of optical channel modules 30 to rotate.

The lifting module 80 includes a lifting frame 810 and an actuator 820 connected to the lifting frame 810. The rotating frame 610 of the rotating module 60 is disposed at the lifting frame 810. As the actuator 820 drives the lifting frame 810 to move up and down, the lifting frame 810 drives the rotating module 60 to move up and down. The rotating module 60 also drives the carrying base 10, the rotating member 20, and the plurality of optical channel modules 30 to move up and down.

Furthermore, the light-source module 90 is connected to the plurality of optical channel assemblies 330 providing the detection light source. The light-source module 90 provides the detection light source to the plurality of optical channel assemblies 330, so that the plurality of optical channel assemblies 330 can emit the detection light source. The photodetection module 70 includes at least a photoreceiver 710. The rest of the plurality of optical channel assemblies 330 are connected to the photoreceiver 710. The plurality of optical channel assemblies 330 connected with the photoreceiver 710 receive and transmit the reflected detection light source to the photoreceiver 710 and thus further performing analysis according to the reflected detection light sources received by the photoreceiver 710.

Figure 5:
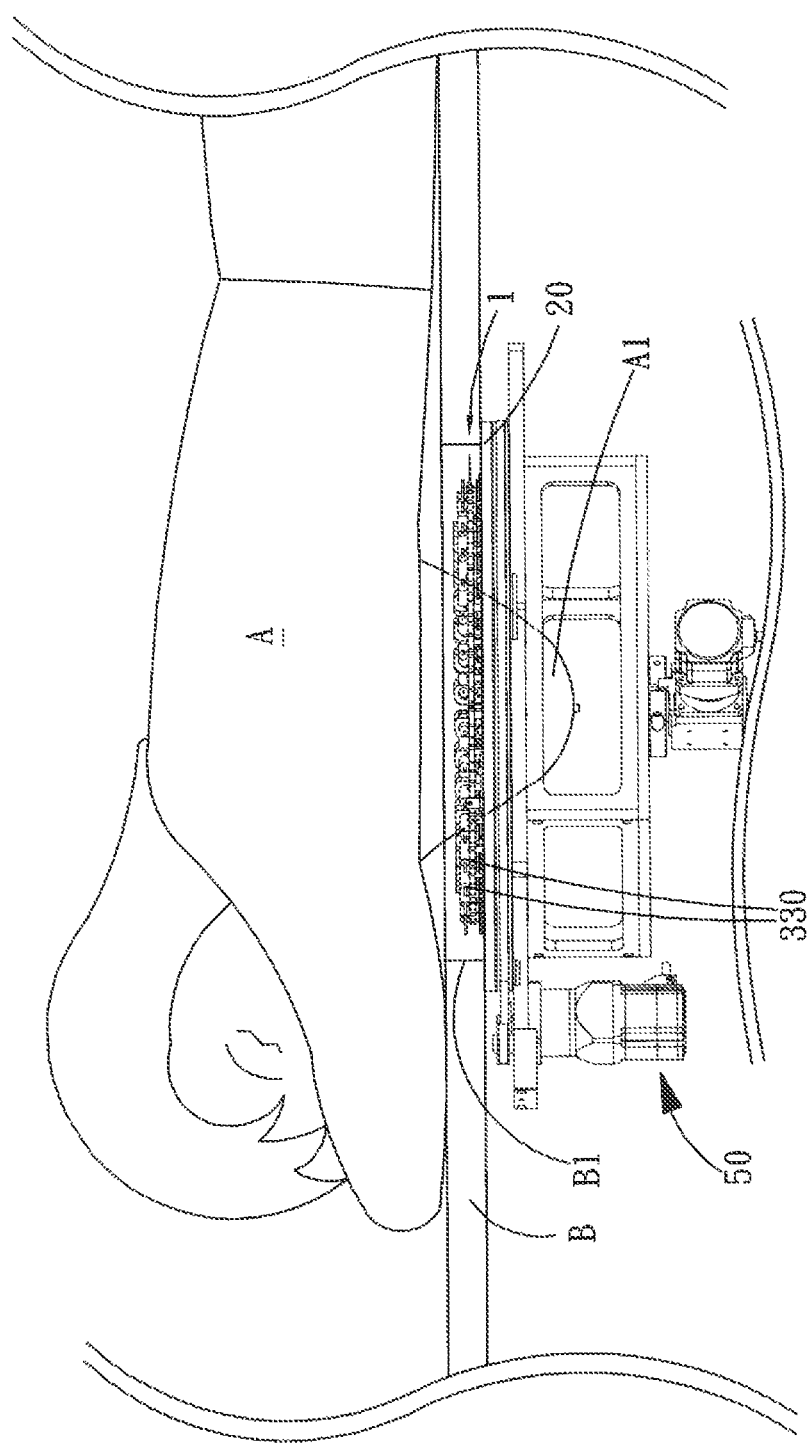
FIG. 5 shows a usage status diagram of the optical tomography scanning and imaging system according the second embodiment of the present invention.

Please refer to FIG. 5, which shows a usage status diagram of the optical tomography scanning and imaging system according the second embodiment of the present invention. Here, the examination for breast cancer is used for description. Normally, the examination for breast cancer adopts the prone diffuse optical tomography, for breast. Thereby, the optical tomography scanning and imaging system 2 according to the present embodiment further comprises a bed B. The bed B includes a hole B1. The annular scanning device 1 is disposed under the bed B. The second hole 210 and the first hole 110 of the annular scanning device 1, as shown in FIG. 1B, correspond to the hole B1 of the bed B. When the optical tomography scanning and imaging system 2 according to the present embodiment is operating, an examinee A lies prone on the bed B. An object under test A1 (the breast) of the examinee A is placed in the first hole 110 and the second hole 210 through the hole B1. Namely, the object under test A1 is placed in a scanning region of the annular scanning device 1. The scanning region is formed by the plurality of optical channel assemblies 330. In addition, the scanning region only scans a portion of the object under test A1.

Then, the distance between the plurality of optical channel assemblies 330 and the object under test A1 is adjusted. The driving module 50 drives the rotating member 20 to rotate and make the plurality of optical channel assemblies 330 to move towards the object under test A1. Next, the plurality of sensing members 40 are used for sensing the distance between the plurality of optical channel assemblies 330 and the object under test A1 until the distance between the plurality of optical channel assemblies 330 and the object under test A1 is a proper detection distance. The plurality of sensing members 40, as shown in FIG. 1B, transmits the control signal to the driving module 50, which stops operation according to the control signal for maintaining the distance between the plurality of optical channel assemblies 330 and the object under test A1 to the proper detection distance. Thereby, the shape of the object under test A1 can be confirmed for future image reconstruction.

According to the present embodiment, the proper detection distance means that the first end 3301 of each optical channel assembly 330, as shown in FIG. 3A, does not contact the object under test A1 or only contact the object under test A1 slightly for maintaining comfort of the examinee A during the process of examination. In addition, the distance between the first end 3301 of the optical channel assembly 330 and the object under test A1 cannot be overly large. Thereby, the optical signal received by each optical channel assembly 330 can produce clear scanning images.

After the locations of the plurality of optical channel assemblies 330 are adjusted, the light-source module 90 transmits a optical transmitting signal to the corresponding plurality of optical channel assemblies 330, which transmit the detection light source to the object under test A1. The detection light source is formed by light sources of multiple wavelengths. After the object under test A1 reflects the detection light source, the plurality of optical channel assemblies 330 not transmitting the detection light source receive the detection light source reflected from the object under test A1 and transmits it to the photoreceiver 710.

The rotating module 60 drives the carrying base 10 to rotate. The carrying base 10 drives the rotating member 20 having the plurality of optical channel assemblies 330 to rotate. Thereby, the locations of the plurality of optical channel assemblies 330 providing the detection light sources are changed for providing the detection light sources to the object under test A1 at different locations and thus acquiring the reflected detection light sources by the object under test A at different illuminating locations. Then, according to the plurality of detection light sources reflected by the object under test A1, the tissue image of the object under test A1 corresponding to the scanning region can be generated.

In order to acquire the tissue image of the entire object under test A1, the lifting module 80 can be used for adjusting the scanning regions formed by the plurality of optical channel assemblies 330. Then the above steps are repeated for completing the examination of the entire object under test A1. Finally, the tissue image of the entire object under test A1 is given. The optical tomography scanning and imaging system 2 according to the present embodiment can rotate about the annular scanning device 1 and scan the object under test A1 horizontally and then move up and down along the center of the annular scanning device 1 for scanning the object under test A1 horizontally at different depths. In other words, three-dimensional scanning and examination on the object under test A1 can be performed.

To sum up, the present invention provides an annular scanning device for optical tomography scanning and imaging system. The plurality of optical channel assemblies can control the distance between the plurality of optical channel assemblies and the object under test according to the size of the examinee's object under test, so that the plurality of optical channel assemblies will not contact directly the object under test or simply contact the object under test slightly. Thereby, the examinee will not feel uncomfortable or unsafe during the process of examination. In addition, the accuracy of examination can be improved as well. Moreover, the plurality of optical channel modules can be disassembled from the rotating member rapidly. They can be assembled to the rotating member with ease. Consequently, the disposition of the plurality of optical channel modules can be adjusted real-timely, which enhances convenience in usage.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

The invention claimed is:

1. An annular scanning device comprising:
   a carrying base, having a first hole and a plurality of guiding grooves, and said plurality of guiding grooves disposed annularly about said first hole on said carrying base;
   a rotating member, disposed on said carrying base, having a second hole and a plurality of positioning openings, said second hole corresponding to said first hole, and said plurality of positioning openings corresponding to said plurality of guiding grooves, respectively;
   a plurality of optical channel modules, disposed between said plurality of positioning openings on said rotating member, having an optical channel assembly and a sliding base, respectively, said optical channel assembly disposed on said sliding base, and one end of said sliding base corresponding to said positioning opening and said guiding groove; and
   a driving module, disposed on said carrying base and connected with said rotating member, driving said rotating member to rotate, said rotating member driving a plurality of sliding bases to slide on said rotating member, and said plurality of sliding bases driving a plurality of optical channel assemblies to move close to or away from a direction of said second hole.

2. The annular scanning device of claim 1, further comprising a plurality of sensing members, disposed at two or more of said optical channel modules, a sensing end of each sensing member orienting towards said second hole, and said sensing end aligning with an end of said optical channel assembly orienting towards said second hole.

3. The annular scanning device of claim 1, wherein said driving module comprises an actuator disposed on said carrying base and connected with said rotating member.

4. The annular scanning device of claim 3, wherein said driving module further comprises a transmission structure connected with said actuator and said rotating member; said actuator drives said transmission structure; and said transmission structure drives said rotating member to rotate.

5. The annular scanning device of claim 4, wherein said transmission structure comprises a first transmission member disposed at said actuator and connected with said rotating member.

6. The annular scanning device of claim 5, wherein said transmission structure further comprises a second transmission member connected with said first transmission member and said rotating member.

7. The annular scanning device of claim 1, wherein said optical channel module further comprises a plurality of sliding tracks, disposed between said plurality of positioning openings on said rotating member, and one end said plurality of sliding bases disposed on said plurality of sliding tracks.

8. The annular scanning device of claim 7, wherein each of said sliding bases comprises:
   a sliding block, disposed on the corresponding sliding track;
   a base body, disposed at said sliding block, and said optical channel assembly disposed on said base body; and
   a guiding pillar, disposed at said base body, and passing through the corresponding one of said positioning openings and moving along corresponding one of said guiding grooves.

9. The annular scanning device of claim 8, wherein said sliding base further comprises a fixing member disposed on said base body and fixing said optical channel assembly.

10. The annular scanning device of claim 1, and further comprising a rotating module disposed on said carrying base for driving said carrying base to rotate.

11. The annular scanning device of claim 10, wherein said rotating module comprises:
    a rotating frame, disposed at said carrying base; and
    an actuator, connected with said rotating frame.

12. The annular scanning device of claim 10, and further comprising a lifting module, disposed at said rotating module for driving said rotating module and said carrying base to move up and down.

13. The annular scanning device of claim 12, wherein said lifting module comprises:
    a lifting frame, disposed at said rotating module; and
    an actuator, connected with said lifting frame.

14. The annular scanning device of claim 1, further comprising:
    a light-source module, connected with at least one of said plurality of optical channel assemblies; and
    a photodetection module, including at least one photoreceiver, said at least one photoreceiver connected with the plurality of optical channel assemblies.

15. The annular scanning device of claim 14, wherein the one or more optical channel assembly connected with said light-source module provides a detection light source including multiple wavelengths.

* * * * *